United States Patent [19]

Ashton et al.

[11] 3,985,717

[45] Oct. 12, 1976

[54] VULCANIZABLE RUBBER COMPOSITIONS COMPRISING ORGANIC DERIVATIVES OF HYDRAZINE

[75] Inventors: Stanley Ashton; Peter Laithwaite; John Anthony Taylor, all of Manchester, England

[73] Assignee: Imperial Chemical Industries Limited, London, England

[22] Filed: Mar. 10, 1975

[21] Appl. No.: 556,819

Related U.S. Application Data

[63] Continuation of Ser. No. 339,762, March 12, 1973, abandoned.

[30] Foreign Application Priority Data

Mar. 22, 1972 United Kingdom............... 13408/72

[52] U.S. Cl. .................... 260/79.5 R; 260/23.7 M; 260/23.7 R; 260/79.5 P; 260/453 R; 260/780
[51] Int. Cl.² .................... C08C 19/20; C08K 5/24; C08K 5/30
[58] Field of Search.................. 260/79.5 P, 79.5 R, 260/780, 23.7 B, 23.7 M

[56] References Cited
UNITED STATES PATENTS

| | | |
|---|---|---|
| 2,762,740 | 9/1956 | Margot et al. ................. 260/453 R |
| 3,178,447 | 4/1965 | Kohn............................... 260/453 R |
| 3,344,153 | 9/1967 | Kühle et al...................... 260/453 R |
| 3,579,460 | 5/1971 | Kerwood........................... 260/780 |
| 3,678,017 | 7/1972 | Shelton et al. .................. 260/453 R |
| 3,703,500 | 11/1972 | Nast et al........................ 260/453 R |
| 3,705,135 | 12/1972 | Wolfinger ....................... 260/453 R |
| 3,839,303 | 10/1974 | D'Amico............................ 260/780 |

*Primary Examiner*—Ronald W. Griffin
*Attorney, Agent, or Firm*—Cushman, Darby & Cushman

[57] ABSTRACT

Hydrazides of sulphenic acids are inhibitors of premature vulcanization of sulphur curable rubbers. The hydrazides are prepared from sulphenyl chlorides or bromides and the appropriate hydrazine in presence of an acid binding agent. The most effective hydrazides are those from secondary alkyl sulphenyl chlorides or bromides, or those in which the nitrogen atom attached to the sulphenic acid group also carries an acyl group, or in which the other nitrogen atom is attached to an alkylidene or cycloalkylidene group.

7 Claims, No Drawings

VULCANIZABLE RUBBER COMPOSITIONS COMPRISING ORGANIC DERIVATIVES OF HYDRAZINE

This is a continuation of application Ser. No. 339,762, filed Mar. 12, 1973, now abandoned This invention relates to an improved process for the vulcanization of rubbers and more particularly to the use of certain organic derivatives of hydrazine as inhibitors of premature vulcanization.

It is customary in the manufacture of vulcanized rubbers to incorporate into the unvulcanized rubber various additives such as antioxidants, antiozonants, fillers, vulcanization activators, etc., and lastly vulcanization accelerators and a vulcanizing agent such as sulphur. The compounded rubber is then shaped and finally raised to vulcanization temperature. Before the final stage however some premature vulcanization may take place, especially during the compounding stage in a mill or Banbury mixer when heat is generated, or during handling such as calendering or extruding, or in some cases even during storage. Premature vulcanization causes the rubber to become lumpy with the result that subsequent processing or vulcanizing operations cannot be carried out satisfactorily. Premature vulcanization may be reduced by using delayed action accelerators of for example the benzthiazylsulphenamide type and also by the use of retarders such as N-nitrosodiphenylamine or salicylic acid, but these retarders frequently introduce other difficulties. No satisfactory means of preventing premature vulcanization has hitherto been found and the increasing use of furnace carbon blacks and of antioxidants and antiozonants based on p-phenylenediamine has exacerbated the problem. It has now been found that certain organic hydrazine derivatives are powerful inhibitors of premature vulcanization.

According to the invention there is provided a process for reducing the premature vulcanization of a rubber containing a vulcanizing agent and a vulcanization accelerator which comprises incorporating in the rubber a hydrazine derivative of the formula

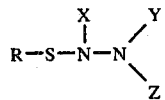

wherein R is an optionally substituted alkyl, cycloalkyl, alkenyl or aryl group, X is an acyl group or a group of the type represented by R, Y and Z, which may be the same or different, are each a group of the type represented by X or a hydrogen atom or may together represent an optionally substituted alkylidene or cycloalkylidene group or may together with the attached nitrogen atom form a heterocyclic ring or, Y and Z together with X and the two nitrogen atoms may form a heterocyclic ring, provided that both X and Y are not carboalkoxy groups when Z is a hydrogen atom.

R must not represent an aliphatic group containing two or more halogen atoms on the carbon atom attached to the sulphur atom. As examples of groups which may be represented by R there are mentioned methyl, ethyl, n-propyl, iso-propyl, n-butyl sec-butyl, iso-butyl, tert-butyl, n-hexyl, n-octyl, tert-octyl, n-dodecyl, tert-dodecyl, or tert-hexadecyl, allyl, cyclohexyl, phenyl, β-naphthyl, 4-methoxyphenyl, 4-ethoxyphenyl, 4-dimethylamino phenyl, 4-chlorophenyl, 2-ethoxycarbamylphenyl, benzyl, β-ethoxyethyl or ethoxycarbonylmethyl. R is preferably alkyl, particularly secondary alkyl such as iso-propyl or sec-butyl or cyclohexyl.

As acyl groups which may be represented by X there are mentioned for example acetyl, chloroacetyl, dichloroactyl, trichloroacetyl, benzoyl, 3-nitrobenzoyl, 4-methoxybenzoyl, β-naphthoyl, propionyl, butyroyl, hexanoyl, methanesulphonyl, benzenesulphonyl, β-naphthylsulphonyl, dimethylcarbamoyl, diethylcarbamoyl, diphenylcarbamoyl, dimethylsulphamoyl, diethylsulphamoyl and diphenylsulphamoyl.

As alkylidene or cycloalkylidene groups which may be represented by Y and Z there are mentioned for example methylidene, ethylidene, n-butylidene, iso-butylidene, iso-propylidene, cyclohexylidene, benzylidene, diphenylmethylidene, 3-nitrobenzylidene, and 4-methoxybenzylidene.

As heterocyclic rings which may be formed from Y, Z and the nitrogen atom there are mentioned for example morpholine, piperidine, hexamethyleneimine, caprolactam, pyrrolidone, succinimide, phthalimide and tetrahydrophthalimide, and as heterocyclic rings which may be formed from Y, or Y and Z, X and the two nitrogen atoms there are mentioned for example 3-phenylpyrazol-5-one, 3-methylpyrazol-5-one, 3-methylpyridazone, 3-phenylpyridazone, phthalhydrazide, tetrahydrophthalhydrazide and succinhydrazide.

X is preferably an acyl group for example acetyl, benzoyl, 3-nitrobenzoyl or dimethylcarbamoyl.

Y and Z preferably together represent an alkylidene group for example benzylidene, 3-nitrobenzylidene, 4-methoxybenzylidene, diphenylmethylidene or diisopropylidene or a cycloalkylidene group such as cyclohexylidene.

The groups represented by X, Y and/or Z may contain as substituents one or more groups of the formula R—S—, and the corresponding hydrazine derivatives containing more than one group of the formula R-S- are usually especially effective inhibitors of premature vulcanization. Examples of such compounds are 1,4,4-tris(alkylthio)pyrazolones such as 3-phenyl-1,4,4-tris-(isopropylthio)pyrazolone.

The vulcanizing agent used in the process of the invention may be a sulphur donor, such as N,N'-dithiobis-morpholine, N,N'-dithiobis-caprolactam, tetramethylthiuram disulphide, diethylthiophosphenyl disulphide or diethylthiophosphenyl trisulphide or preferably elemental sulphur, or for example a peroxide or other type of vulcanizing agent.

The vulcanization accelerator used in the process of the invention is preferably a sulphenamide such as N-cyclohexylbenzothiazole- 2-sulphenamide, N-t-butylbenzothiazole-2-sulphenamide, N-diethyleneoxybenzothiazole-2-sulphenamide or N-dicyclohexylbenzothiazole-2-sulphenamide, a thiazole such as mercaptothiazole, 2-mercaptobenzothiazole or dibenzothiazyl disulphide or a thiuram such as tetramethylthiuram monosulphide, tetramethylthiuram disulphide, tetramethylthiuram tetrasulphide, tetraethylthiuram monosulphide, tetraethylthiuram disulphide, or a metal salt of a dithiocarbamate such as zinc dimethyldithiocarbamade or sodium diethydithiocarbamate.

Other types of accelerators may however be used such as diaryl guanidines, thioureas, xanthates or aldehyde-amine condensates, or mixtures of any of these and the above accelerators.

The amount of vulcanization accelerator may be that conventionally used in the manufacture of rubber vulcanizates, for exampl from 0.5 to 6.0% of the weight of the rubber.

The amount of hydrazine derivative is conveniently from 0.05 to 5.0% of the weight of the rubber.

Rubbers which may be used in the process of the invention include both natural and synthetic rubbers and mixtures thereof. The synthetic rubber may in general be any polymeric material containing olefinic unsaturation and capable of being cross-linked by for example sulphur, peroxide or other cross-linking agents. Examples of synthetic rubbers include cis-polybutadiene, butyl rubber, ethylene-propylene ter-polymer, polymers of 1,3-butadienes such as isoprene and chloroprene and copolymers of 1,3-butadiene with other monomers such as styrene, acrylonitrile and isobutylene.

The hydrazine derivative may be incorporated into the rubber mix by any conventional procedure, for example on a rubber mill or in an internal mixer.

The rubber mix may also contain conventional rubber adjuvants such as antioxidants, antiozonants, fillers, peptizing agents, pigments, blowing agents, and accelerator activators such as zinc oxide and stearic acid.

The invention is of particular value when the rubber mix is reinforced with a furance black or contains a p-phenylene diamine-based antiozonant since such rubber mixes are especially prone to premature vulcanization.

The hydrazine derivatives used in the process of the invention are new compositions of matter, and this represents a further feature of the invention.

The hydrazine derivatives may be prepared from the appropriate sulphenyl chlorides or bromides and appropriate hydrazine or derivative thereof in presence of an acid binding agent such as a tertiary amine, preferably in an inert solvent, or from the sulphenyl chloride or sulphenyl bromide and an alkali metal salt of the hydrazine or derivative thereof in those cases where such a salt can be obtained as for example when X is an acyl group.

In those cases in which the hydrazine or derivative thereof contains, apart from the NH group, other groups containing labile hydrogen atoms further groups of the formula R—S— may replace these hydrogen atoms during the preparative process. For example pyrazolones may afford 1,4,4-tristhio derivatives by reaction at both the NH group and the active methylene group.

By the process of the invention there are obtained vulcanizable rubber compositions which can be handled on conventional rubber processing machines or stored for long periods with little tendency to premature vulcanization but which will cure readily at conventional vulcanization temperatures to give vulcanizates of excellent physical properties. These unvulcanized rubber compositions, their vulcanization by heating to vulcanization temperatures, and the vulcanizates so obtained are further features of this invention.

The invention is illustrated but not limited by the following Examples in which all parts and percentages are by weight unless otherwise stated.

EXAMPLE 1

A solution of 11.1 parts of isopropylsulphenyl chloride in 100 parts of carbon tetrachloride was added at room temperature to a stirred suspension of 16 parts of 3-phenylpyrazol-5-one and 10.1 parts of triethylamine in 100 parts of carbon tetrachloride. The mixture was stirred for 2 hours at room temperature and then kept overnight. The precipitated triethylamine hydrochloride and unchanged 3-phenylpyrazol-5-one were filtered off. The filtrate was evaporated to leave a red oil which was triturated with methylated spirits to yield 3.9 parts of 1,4,4-tris(isopropylthio)-3-phenylpyrazol-5-one, melting at 66°–67°. Analysis: Calculated for $C_{18}H_{26}N_2S_3O$, C = 56.5; H = 6.8; N = 7.3; S = 25.1%. Found: C = 57.1; H = 6.9; N = 7.2; S = 22.2%. The N.M.R. spectrum was consistant with the proposed structure.

EXAMPLE 2

A solution of 12.05 parts of isopropylsulphenyl chloride in 50 parts of carbon tetrachloride was added dropwise at 25°–30° C to a stirred slurry of 20.5 parts of 3-(m-nitrophenyl)pyrazol-5-one and 10 parts of triethylamine in 50 parts of carbon tetrachloride. The mixture was stirred at 25° for a further 30 minutes, triethylamine hydrochloride and excess 3-(m-nitrophenyl)-pyrazol-5-one were removed by filtration and the filtrate evaporated to leave 7.3 parts of 1,4,4-tris-(isopropylthio)-3-(m-nitrophenyl)pyrazol-5-one as pale buff plates, melting at 73°–74°. Analysis: Found: C = 50.3; H = 5.9; N = 9.8; S = 22.2%. $C_{18}H_{25}N_3O_3S_3$ requires C = 50.6; H = 5.85; N = 9.8; S = 22.5%.

EXAMPLE 3

A solution of 11.1 parts of isopropylsulphenyl chloride in 100 parts of carbon tetrachloride was added to a stirred suspension of 19 parts of 3-(4-methoxy)phenyl-pyrazol-5-one and 10.1 parts of triethylamine in 100 parts of carbon tetrachloride at room temperature. The mixture was stirred for a further 1 hour at room temperature. The precipitated triethylamine hydrochloride was filtered off and the remaining yellow solution evaporated to leave an orange oil which was purified by chromatography over silica gel. Elution with carbon tetrachloride gave 9 parts of 1,4,4-tris-(isopropylthio)-3-(4'-methoxyphenyl)pyrazol-5-one as a white solid of melting point 52°–54° C. Analysis: Calculated for $C_{19}H_{28}O_2N_2S_3$: N = 6.8; S = 23.3%. Found: N = 6.5; S = 23.4%. The N.M.R. spectrum was consistent with the proposed structure.

EXAMPLE 4

A solution of 11.1 parts of isopropylsulphenyl chloride in 50 parts of carbon tetrachloride was added dropwise to a stirred suspension of 17.5 parts of N-acetyl-N-(3'-nitrobenzylidene) hydrazone and 10.1 parts of triethylamine in 100 parts of dimethyl formamide at room temperature. The reaction was mildly exothermic and after stirring for a further hour 300 parts of water were added and the resulting mixture was extracted twice with 100 parts of carbon tetrachloride. The carbon tetrachloride extracts were washed with water, dried, and the solvent evaporated off to yield a yellow solid which was crystallized from aqueous ethanol to yield 10 parts of N-isopropylthio-N-acetyl-N'-3-nitrobenzylidene hydrazone of melting point 82°–3° C. Analysis: Calculated for $C_{12}H_{15}N_3O_3S$: C = 52.1; H = 5.3; N = 14.9; S = 11.4%. Found: C = 51.4; H = 5.1; N = 14.6; S = 11.3%. The NMR spectrum was consistant with the proposed structure.

EXAMPLE 5

A solution of 11.1 parts of isopropylsulphenyl chloride in 50 parts of carbon tetrachloride was added to a stirred solution of 16.2 parts of N-acetyl-N'-benzylidene hydrazone and 10.1 parts of triethylamine in 100 parts of carbon tetrachloride at 0°–5° C. The mixture was stirred for a further 1 hour. Precipitated triethylamine hydrochloride was filtered off and solvent removed under reduced pressure to yield 23.7 parts of a yellow oil. Analysis: Calculated for $C_{12}H_{16}ON_2S$: $C = 61.0$; $H = 6.8$; $N = 11.9$; $S = 13.6\%$. Found: $C = 61.1$, $H = 6.8$; $N = 12.0$; $S = 13.8\%$. The NMR spectrum was consistent with the above structure.

EXAMPLE 6

A solution of 12.45 parts of n-butylsulphenyl chloride in 50 parts of carbon tetrachloride was added to a stirred suspension of 22.4 parts of N-benzoyl-N'-benzylidene hydrazone and 10.1 parts of triethylamine in 100 parts of carbon tetrachloride at 0°–5° C. The mixture was stirred for a further 1 hour at room temperature, triethylamine hydrochloride was filtered off and the solution was evaporated, leaving a yellow oil which was purified by column chromatography to yield 18 parts of an oil. This oil was titurated with petroleum ether, b.p. 30°–40°, to yield 15.1 parts of -N-benzoyl-N-n-butylthio-N'-benzylidene hydrazone as a colorless solid melting at 50°. Analysis: Calculated for $C_{18}H_{20}ON_2S$: $C = 69.23$; $H = 6.41$; $N = 8.97$; $S = 10.26\%$. Found: $C = 67.9$; $H = 6.5$; $N = 9.2$; $S = 11.2\%$. The NMR spectrum was consistent with the above structure.

EXAMPLE 7

A solution of 12.05 parts of isopropylsulphenyl chloride in 50 parts of carbon tetrachloride was added to a stirred mixture of 10 parts of triethylamine and 26 parts of N-benzenesulphonyl-N'-benzylidene hydrazone in 50 parts of carbon tetrachloride. After stirring for 30 minutes at room temperature insoluble material is removed and the filtrate evaporated under reduced pressure to leave 31.2 parts of a sticky solid which on crystallization from ethyl acetate gives 16.5 parts of N-isopropylthio-N-benzenesulphonyl-N'-benzylidene hydrazone as colorless needles, melting at 117°–121°. Analysis: Found: $C = 57.2$; $H = 5.5$; $N = 8.1$; $S = 18.9\%$. $C_{16}H_{18}N_2O_2S_2$ requires $C = 57.5$; $H = 5.4$; $N = 8.4$; $S = 19.2\%$.

EXAMPLE 8

A solution of 11.1 parts of isopropylsulphenyl chloride in 50 parts of carbon tetrachloride was added to a stirred suspension of 22.4 parts of N-benzoyl-N'-benzylidene hydrazone and 10.1 parts of triethylamine in 100 parts of carbon tetrachloride at 0°–5° C. The mixture was stirred for a further 1 hour at room temperature, triethylamine hydrochloride was removed and the remaining yellow solution was evaporated to leave a fawn colored solid, which was crystallized from petroleum ether, b.pt. 100°–120°, to yield 18.7 parts of a white solid melting at 102°–103° C. Analysis: Calculated for $C_{17}H_{18}N_2OS$: $C = 68.5$; $H = 6.0$; $N = 9.4$; $S = 10.7\%$. Found: $C = 68.5$; $H = 5.6$; $N = 9.7$; $S = 11.8\%$. The N.M.R. spectrum was consistent with the required structure.

EXAMPLE 9

The following compounds were prepared by the general procedure of Example 1.

N-acetyl-N-isopropylthio-N'-4-methoxybenzylidene hydrazone, yellow oil, analysis: Calculated for $C_{13}H_{18}O_2N_2S$: $C = 58.6$; $H = 6.8$; $N = 10.5$; $S = 12.0\%$. Found: $C = 57.0$; $H = 6.5$; $N = 10.7$; $S = 13.5\%$. The N.M.R. spectrum was consistent with the proposed structure.

N-benzoyl-N-phenylthio-N'-benzylidene hydrazide, melting at 81° C, analysis: calculated for $C_{20}H_{16}ON_2S$: $C = 72.3$; $H = 4.8$; $N = 8.4$; $S = 9.6\%$. Found: $C = 72.3$; $H = 5.1$; $N = 8.8$; $S = 8.8\%$. The N.M.R. spectrum was consistent with the proposed structure.

N-acetyl-N-phenylthio-N'-benzylidene hydrazide. The N.M.R. spectrum was consistent with the proposed structure.

1-isopropylthio-3,5-dimetylpyrazolene, a colourless oil, analysis: Found: $C = 56.4$; $H = 9.3$; $S = 19.7\%$. $C_8H_{14}N_2S$ requires $C = 56.5$; $H = 8.2$; $S = 18.8\%$.

N-Benzenesulphonyl-N-isopropylthio-N'-3-nitrobenzylidene hydrazone, a pale yellow solid melting at 120°–121°, analysis: Found: $C = 52.0$; $H = 4.6$; $N = 12.0$; $S = 16.6\%$. $C_{16}H_{17}N_3O_4S_2$ requires $C = 50.7$; $H = 4.5$; $N = 11.1$; $S = 16.9\%$.

N-Benzenesulphonyl-N-isopropylthio-N'-4-methoxybenzylidene hydrazone, a colourless solid melting at 107°–108° C, analysis: Found: $C = 55.9$; $H = 5.6$; $N = 8.6$; $S = 17.7\%$. $C_{17}H_{20}N_2O_3S_2$ requires $C = 56.0$; $H = 5.5$; $N = 7.7$; $S = 17.6\%$.

N-Benzenesulphonyl-N-t-butylthio-N'-3-nitrobenzylidene hydrazone, a pale yellow solid melting at 119°–126° C, analysis: Found: $C = 50.6$; $H = 4.7$; $N = 10.3$; $S = 17.1\%$. $C_{17}H_{19}N_3O_4S_2$ requires $C = 51.9$; $H = 4.8$; $N = 10.7$; $S = 16.3\%$.

N-Benzenesulphonyl-N-t-butylthio-N'-4-methoxybenzylidene hydrazone, a colourless solid melting at 119°–120° C, analysis: Found: $N = 7.5$; $S = 16.8\%$. $C_{18}H_{22}N_2O_3S_2$ requires $N = 7.4$; $S = 16.9\%$.

N-Benzenesulphonyl-N-tert.-butylthiobenzylidene hydrazone, colourless prisms m.p. 120°–122°. Found : C, 57.8; H, 5.8; N, 7.9; S, 18.8%. $C_{17}H_{20}N_2O_2S_2$ requires C, 58.6; H, 5.8; N, 8.0; S, 18.4%.

N-p-chlorobenzyl-N-isopropylthiobenzylidene hydrazone, a colourless solid, m.p. 74°. Found : N, 8.7; S, 9.4%. $C_{17}H_{17}Cl\ N_2OS$ requires N, 8.4; S, 9.6%.

N,N-Diphenyl-$N^1$-acetyl-$N^1$-isopropylthiohydrazine, a colourless solid, m.p. 90°–94°. Found : C, 67.7; H, 6.8; N, 10.1; S, 10.6%. $C_{17}H_{20}N_2OS$ requires C, 68.0; H, 6.7; N, 9.3; S, 10.6%.

1-Isopropylthio-3-methyl-4,4-dichloropyrazol-5-one, a pale brown oil purified by chromatography over silica gel. Found : Cl, 30.9; N, 12.2; S, 13.4%. $C_7H_{10}Cl_2N_2OS$ requires Cl, 29.5; N, 11.6; S, 13.3%.

1-Isopropylthio-3-phenyl-4,4-dichloropyrazol-5-one, a pale yellow solid, m.p. 62°. Found : C, 46.8; H, 4.4; N, 8.8; S, 10.7%. $C_{12}H_{12}Cl_2N_2OS$ requires C, 47.5; H, 4.0; N, 9.2; S, 10.6%.

N-p-Nitrobenzoyl-N-isopropylthiobenzylidene hydrazone, a pale yellow solid m.p. 142°–143°. Found : C, 60.7; H, 5.2; N, 12.7; S, 9.3%. $C_{17}H_{17}N_3O_3S$ requires C, 59.5; H, 5.0; N, 12.2; S, 9.3%.

N-Acetyl-N-isopropylthio-n-butylidene hydrazone, a colourless oil purified by chromatography over silica gel.

N-Acetyl-N-isopropylthio-isobutylidene hydrazone, a colourless oil purified by chromatography over silica gel.

N-Formyl-N-isopropylthiobenzylidene hydrazone, a colourless solid, m.p. 37.5°–38.5°.

N-Benzoyl-N-isopropylthio-n-butylidene hydrazone, a colourless oil purified by chromatography over silica gel.

EXAMPLE 10

Rubber mixes of the following compositions were prepared by blending the components on a rubber mill.

| | |
|---|---|
| Natural rubber, smoked sheet | 100 |
| High abrasion furnace carbon black | 45 |
| Zinc oxide | 3.5 |
| Stearic acid | 3.0 |
| Hydrocarbon softener | 3.5 |
| Sulphur | 2.5 |
| N-cyclohexylbenzothiazole-2-sulphenamide | 0.5 |
| Hydrazine derivative | As listed in Table I |

The rubber mixes were tested for Mooney scorch time at 120° C by means of a Mooney plastomer, the time being expressed as time in minutes required by the reading to rise to 10 units above the minimum viscosity, and for cure time by means of an Oscillating Disc Rheometer, the time ($T_{95}$) being expressed as that required to obtain a modulus which is 95% of the maximum modulus torque (R.M.T.) itself expressed in rheometer units. The results are given in Table I.

TABLE I

| HYDRAZONE DERIVATIVE | | | | | | | |
|---|---|---|---|---|---|---|---|
| N-acetyl-N-t-butylthio-N'-4-methoxybenzylidene hydrazone | — | 0.25 | — | — | — | — | — |
| N-acetyl-N-isopropylthio-N'-3-nitrobenzylidene hydrazone | — | — | 0.25 | — | — | — | — |
| N-acetyl-N-isopropylthio-N'-4-methoxybenzylidene hydrazone | — | — | — | 0.25 | — | — | — |
| N-benzoyl-N-phenylthio-N'-benzylidene hydrazone | — | — | — | — | 0.25 | — | — |
| N-benzoyl-N-isopropylthio-N'-benzylidene hydrazone | — | — | — | — | — | 0.25 | — |
| N-acetyl-N-isopropylthio-N'-benzylidene hydrazone | — | — | — | — | — | — | 0.25 |
| Mooney Scorch at 120° C $t_{10}$ | 24 | 30 | 45 | 43 | 34 | 41 | 41 |
| Rheometer at 150 = C $T_{95}$ | 20.0 | 25.0 | 24.0 | 22.4 | 20.8 | 22.5 | 22.5 |
| R.M.T. | 57 | 55 | 55 | 55 | 57 | 58 | 58 |

EXAMPLE 11

The procedure of Example 10 is repeated using the hydrazine derivatives listed in Table II which gives the results obtained.

TABLE II

| HYDRAZINE DERIVATIVE | | | | | | |
|---|---|---|---|---|---|---|
| N-benzenesulphonyl-N-isopropylthio-N'-benzylidene hydrazone | — | 0.25 | — | — | — | — |
| N-benzenesulphonyl-N-t-butylthio-N'-benzylidene hydrazone | — | — | 0.25 | — | — | — |
| N-benzoyl-N-t-butylthio-N'-benzylidene hydrazone | — | — | — | 0.25 | — | — |
| N-benzoyl-N-n-butylthio-N'-benzylidene hydrazone | — | — | — | — | 0.25 | — |
| 3-phenyl-1,4,4-tris(isopropylthio)pyrazolone | — | — | — | — | — | 0.25 |
| Mooney Scorch at 120° C $t_{10}$ | 25 | 33 | 28 | 35 | 38 | 57 |
| Rheometer at 150° C $T_{95}$ | 18.5 | 20.8 | 19.8 | 19.7 | 20.6 | 23.5 |
| R.M.T. | 62 | 63 | 63 | 64 | 64 | 61 |

EXAMPLE 12

The procedure of Example 10 is repeated using the hydrazine derivatives listed in Tables III and IV giving the Mooney scorch times shown.

TABLE III

| Hydrazine derivative | | | | | | | | |
|---|---|---|---|---|---|---|---|---|
| N-Benzoyl-N-t.-butylthiobenzylidene hydrazone | — | 0.25 | — | — | — | — | — | — |
| N-p-Chlorobenzoyl-N-isopropylthiobenzylidene hydrazone | — | — | 0.25 | — | — | — | — | — |
| N-Acetyl-N-isopropylthio-isobutylidene hydrazone | — | — | — | 0.25 | — | — | — | — |
| N-Acetyl-N-isopropylthio-n-butylidene hydrazone | — | — | — | — | 0.25 | — | — | — |
| N,N-Diphenyl-N¹-acetyl-N¹-isopropylthiohydrazine | — | — | — | — | — | 0.25 | — | — |
| N-Formyl-N-isopropylthiobenzylidene hydrazone | — | — | — | — | — | — | 0.25 | — |
| N-Benzoyl-N-isopropylthio-n-butylidene hydrazone | — | — | — | — | — | — | — | 0.25 | — |
| 1-Isopropylthio-3-phenyl-4,4-dichloropyrazol-5-one | — | — | — | — | — | — | — | 0.25 |
| Mooney Scorch at 120° $t_{10}$ | 22 | 31 | 38 | 42 | 36 | 30 | 42½ | 27 | 32 |

TABLE IV

| Hydrazine derivative | | | | | | |
|---|---|---|---|---|---|---|
| 1,4,4-Tris(isopropylthio-)-3-m-nitrophenylpyrazol-5-one | — | 0.25 | — | — | — | — |
| 1,4,4-Tris(isopropylthio-)-3-p-methoxyphenylpyrazol-5-one | — | — | 0.25 | — | — | — |
| 1-Isopropylthio-3,4,4-trimethylpyrazol-5-one | — | — | — | 0.25 | — | — |
| N-Isopropylthio-N-p-nitrobenzoylbenzylidene hydrazone | — | — | — | — | 0.25 | — |
| N-Isopropylthio-N-benzoylbenzylidene hydrazone | — | — | — | — | — | 0.25 |

TABLE IV-continued

| | | | | | | | |
|---|---|---|---|---|---|---|---|
| 1-Isopropylthio-3-methyl-4,4-dichloropyrazol-5-one | — | — | — | — | — | — | 0.25 |
| Mooney Scorch at 130° $t_{10}$ | 10 | 21¾ | 18½ | 13½ | 17 | 17 | 19¼ |

We claim:

1. A vulcanizable rubber composition containing an unvulcanized, sulfur-curable rubber, a vulcanizing agent for said rubber, a vulcanization accelerator for said rubber composition present in an amount of from 0.5 to 6.0% of the weight of the rubber and a hydrazine derivative present in an amount of from 0.05 to 5.0% of the weight of the rubber and having the formula:

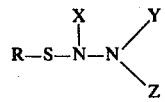

where R is an alkyl, cycloalkyl, alkenyl or aryl group, X is an acyl group, and Y and Z together are methylidene, ethylidene, n-butylidene, isobutylidene, isopropylene, cyclohexylidene, benzylidene, diphenylmethylidene, 3-nitrobenzylidene or 4-methoxybenzylidene.

2. The vulcanizable rubber composition as claimed in claim 1 wherein R is a secondary alkyl group.

3. The vulcanizable rubber composition as claimed in claim 1 wherein R is isopropyl, sec butyl or cyclohexyl.

4. The vulcanizable rubber composition as claimed in claim 1 wherein X is acetyl, benzoyl, 3-nitrobenzoyl or dimethylcarbomoyl.

5. The vulcanizable rubber composition as claimed in claim 1 wherein X is an acyl group derived from a carboxylic acid.

6. The vulcanizable rubber composition as claimed in claim 1 wherein said derivative is N-acetyl-N-isopropylthio-N'-benzylidene-hydrazone.

7. Vulcanizable rubber compositions as claimed in claim 1 wherein the vulcanization accelerator is a sulphenamide thiazole, thiuram or metal salt of a dithiocarbamate.

* * * * *